United States Patent
Osypka et al.

(10) Patent No.: US 7,158,837 B2
(45) Date of Patent: Jan. 2, 2007

(54) LOW PROFILE CARDIAC LEADS

(75) Inventors: Thomas P. Osypka, Palm Harbor, FL (US); Ronald A. Van Den Nieuwenhof, Odessa, FL (US); Mohammed Islam, Palm Harbor, FL (US)

(73) Assignee: Oscor Inc., Palm Harbor, FL (US)

( * ) Notice: Subject to any disclaimer, the term of this patent is extended or adjusted under 35 U.S.C. 154(b) by 411 days.

(21) Appl. No.: 10/619,967

(22) Filed: Jul. 15, 2003

(65) Prior Publication Data
US 2004/0014355 A1    Jan. 22, 2004

Related U.S. Application Data

(63) Continuation-in-part of application No. 10/192,043, filed on Jul. 10, 2002, now Pat. No. 6,978,185.

(51) Int. Cl.
*A61N 1/05* (2006.01)
(52) U.S. Cl. ...................... 607/122; 439/909
(58) Field of Classification Search ............. 607/122, 607/123, 127, 120; 439/909; 600/374, 375
See application file for complete search history.

(56) References Cited

U.S. PATENT DOCUMENTS

| | | | | |
|---|---|---|---|---|
| 5,649,974 A | * | 7/1997 | Nelson et al. | 607/122 |
| 5,676,694 A | * | 10/1997 | Boser et al. | 607/122 |
| 6,289,251 B1 | * | 9/2001 | Huepenbecker et al. | 607/122 |

* cited by examiner

*Primary Examiner*—Kennedy Schaetzle
(74) *Attorney, Agent, or Firm*—Scott D. Wofsy; Edwards Angell Palmer & Dodge LLP

(57) ABSTRACT

A permanent implantable lead having an elongated lead body with a proximal end and a distal end. A multifilar conductor having electrically active elements for providing electrical communication between connectors at the proximal end and electrical components between the proximal and distal ends of the lead body, wherein hulls facilitate resilient, low profile, efficient connection between the multifilar conductor and electrical components and seals secure the position of the electrical components. The hulls are located radially outward of the conductor and radially inward of the electrical components and the seals are located radially outward of the electrical components.

22 Claims, 8 Drawing Sheets

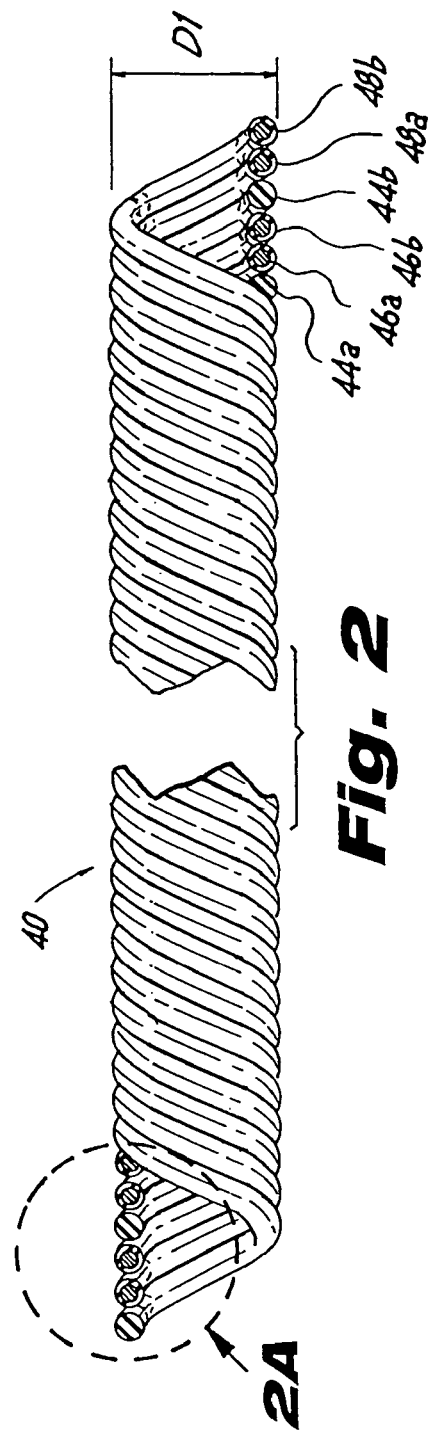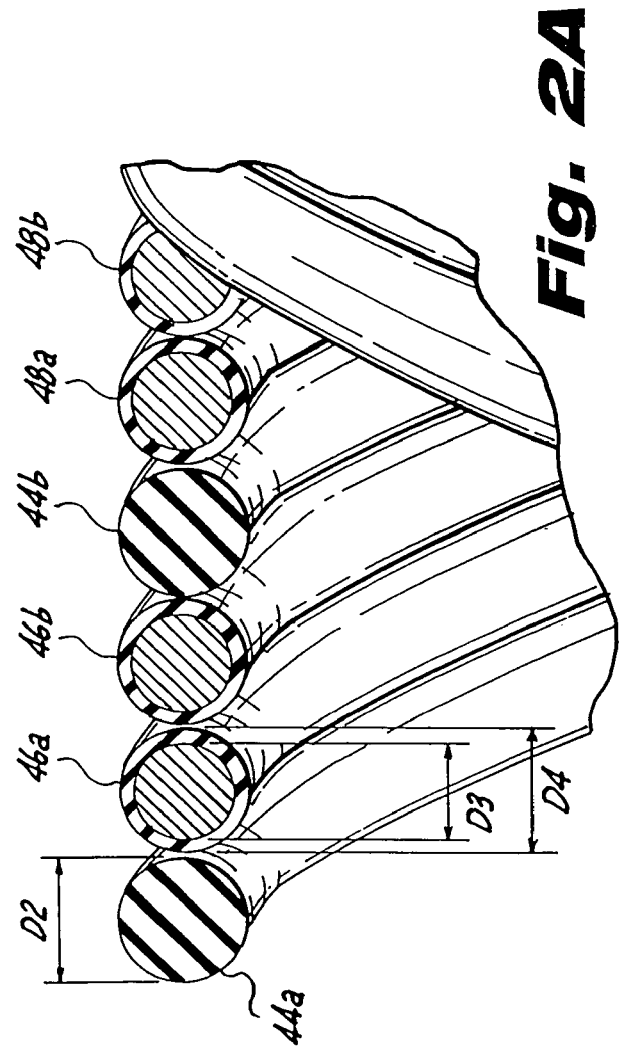

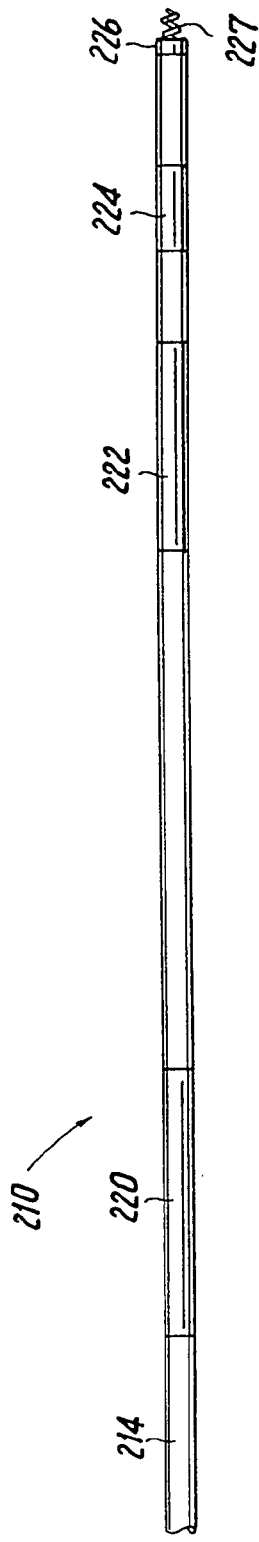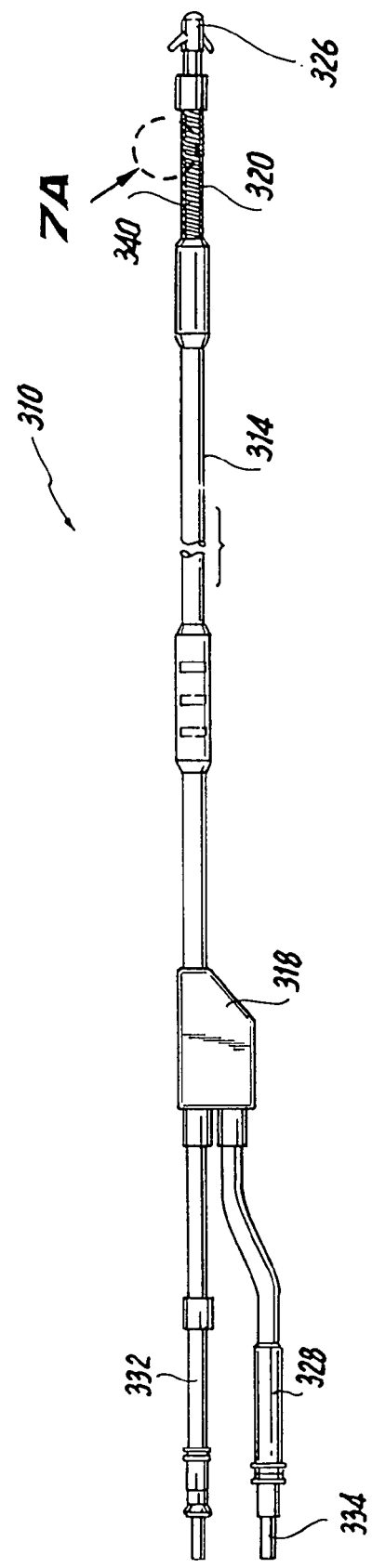

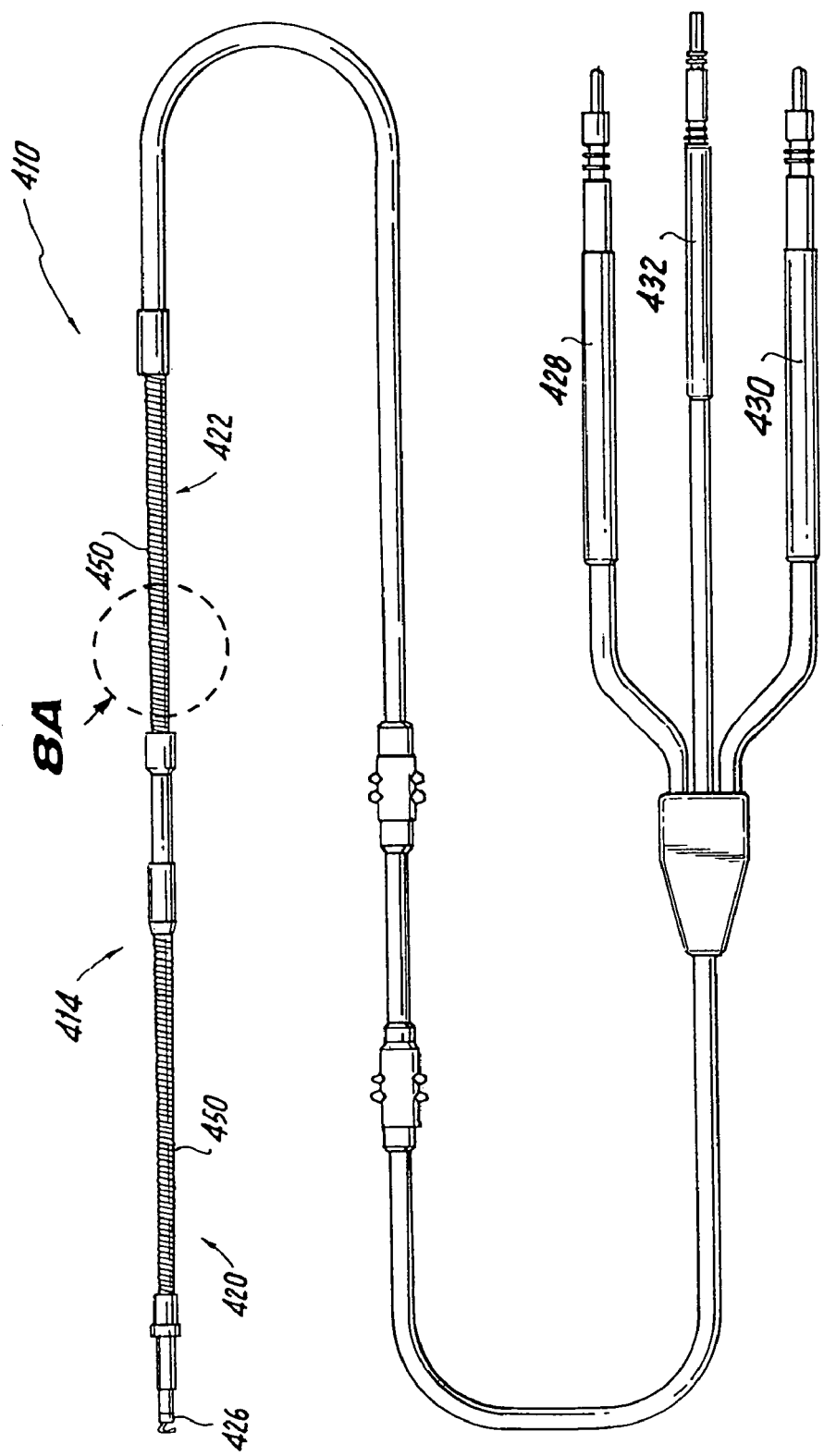

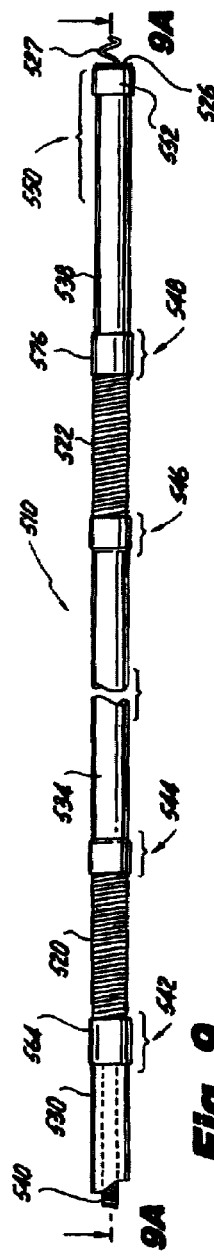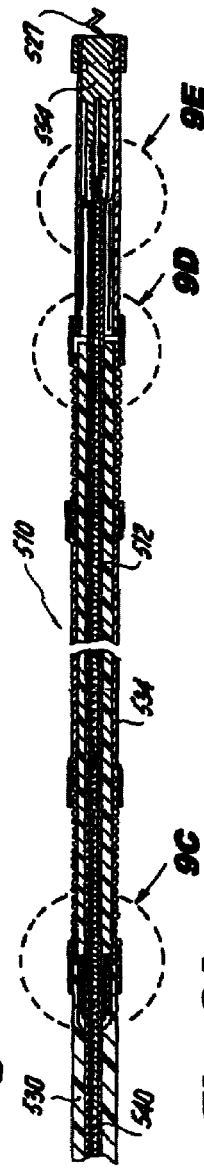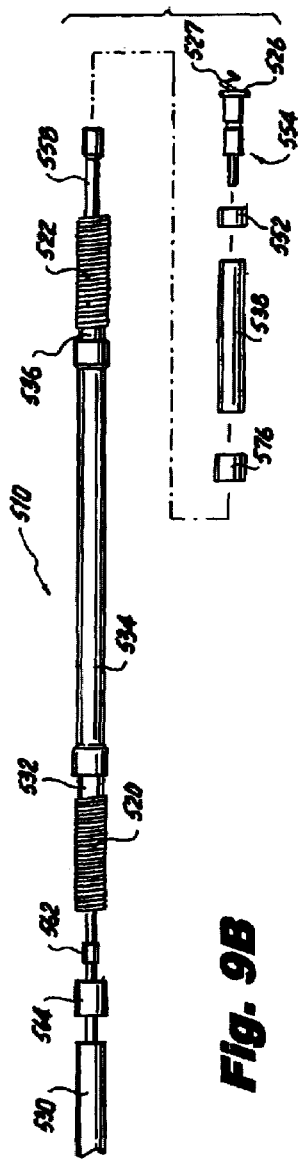

LOW PROFILE CARDIAC LEADS

CROSS-REFERENCE TO RELATED APPLICATION(S)

The subject application is a continuation-in-part of commonly owned, co-pending U.S. patent application Ser. No. 10/192,043, filed Jul. 10, 2002, now U.S. Pat. No. 6,978,185, the disclosure of which is herein incorporated by reference.

BACKGROUND OF THE INVENTION

1. Field of the Invention

The present disclosure relates generally to cardiac pacing and defibrillation leads, and more particularly, to a low profile cardiac leads having a single lumen and a multifilar conductor coil.

2. Background of the Related Art

It is well known in the field of cardiology that certain types of cardiac arrhythmia can be effectively treated by the application of electrical energy to cardiac tissue in an attempt to restore a normal sinus rhythm. Endocardial leads implanted within the heart have been developed to monitor the cardiac state and automatically deliver electrical energy to cardiac tissue. These leads sense the intrinsic rhythm, atrial and ventricular tachycardia and atrial and ventricular fibrillation/flutter.

As used herein, the term ventricular tachycardia refers to any abnormally rapid heart rate (120–180 beats per minute) originating in the ventricles that is generally regular in periodicity and oftentimes is life threatening to the patient. Ventricular fibrillation/flutter is generally a more rapid heartbeat disorder, disorganized and irregular, or non-periodic, and is fatal unless corrected within minutes. Atrial tachycardia and fibrillation/flutter refers to similar abnormal behavior in the atria.

Cardioversion refers to the discharge of electrical energy into the cardiac tissue which may range from a high (40 Joules or more) to a low (less than 1 Joule) energy discharge, but is usually used to describe low energy discharges, typically delivered in the atrium, in an attempt to terminate or revert a tachycardia. Defibrillation usually refers to higher energy electrical discharges, typically delivered to the ventricles, for treating cardiac fibrillation/flutter.

Some leads are designed for defibrillation or pacing but many implantable leads are advantageously fitted for both pacing and defibrillation functions. The typical implantable lead of either arrangement is generally elongated and cylindrical in shape. Thus, for purposes of describing its features, the lead defines two opposing end portions. One end portion (hereinafter referred to as the "distal end"), has various electrodes disposed thereon for sensing heart activity and delivering electrical energy to cardiac tissue. This end is surgically placed adjacent to an inside wall of the heart and is secured at this location either actively with a fixation screw or passively with flexible tines. The other end portion (hereinafter referred to as the "proximal end") is connected by one or more connectors with an implantable device, such as a pacemaker or defibrillator, for monitoring the distal end electrodes and supplying electrical energy.

Under normal conditions, the distal end electrodes are used by the implantable device to monitor the intrinsic electrical activity within the heart. If the implantable device senses abnormal electrical activity, such as that which results from bradycardia, tachycardia or fibrillation, it will respond by directing the appropriate amount of electrical energy to the lead to be discharged by whichever distal end electrodes are necessary to treat the abnormal cardiac activity. Thus, the proper operation of the endocardial lead depends largely on the integrity of electrical communication through the lead.

Multifilar coils constructed of helically wound electrically conductive elements are currently commonly used to convey electrical current through endocardial leads. The conductive elements, or filars, in the multifilar coil are typically constructed from a conductive low resistance material such as MP35N, Elgiloy® or DFT. The multifilar coil gives the advantage of being highly flexible, yet resistant to breakage. Therefore, it is the current standard practice that all permanent implantable leads use coil conductors, usually having 2, 3 or 4 filars, as conveyers of electrical current through the lead. The distal end electrodes may have singular purpose, such as defibrillators or sensors, or the electrodes may have dual functions, such as pacing/sensing or sensing/defibrillation. Depending on the arrangement and amount of electrodes, the leads may have poles requiring one or more sets of anodes and cathodes. However, defibrillation and pacing functions are not usually combined in one electrode. Pacing involves low voltage discharges which have maximum effect when discharged from small surface areas. Defibrillation involves high voltage discharges which are best delivered by electrodes having larger surface areas to avoid possible tissue damage at the electrode interface and higher impedance at the area of discharge.

Current endocardial leads employ various methods for supplying the necessary electricity to the distal end electrodes. One design incorporates two coil conductors of differing diameter arranged coaxially within the lead body to provide the necessary number of electrodes for the components at the distal end. Although the coaxial arrangement may provide enough electricity for multiple components at the distal end, the configuration also possesses considerable disadvantages. For example, to provide electrical integrity between the coils, the inner and outer coil must be insulated relative to one another by an additional nonconductive covering. If the covering is compromised, which is especially possible for long-term lead implantation, electrical communication between vital components will be compromised. Also, the coaxial design increases the diameter of the lead, which may ultimately render potential applications risky or make incorporating all the desired components impossible.

Another lead design currently used incorporates multiple lumens wherein one or more lumens contain coil conductors while another one or more lumens contain low resistance stranded cable. Typically, the coil conductors connect with pacing electrodes while the stranded cables connect with defibrillation electrodes. Although this configuration reduces the potential for electrical crossover between conductors, it increases the profile of the lead and, in turn, the space needed for implantation of the lead, and incorporates the inherently less reliable stranded cable which may break due to fatigue or movement of the lead.

One such multiple lumen design is illustrated in U.S. Pat. No. 5,676,694 to Boser et al. which is incorporated herein by reference. Boser et al. disclose a medical electrical lead having a conductive sleeve 212 for coupling a helical coil 12 to an insulated conductor cable 210. The sleeve 212 completely surrounds the cable 210 and is crimped thereto. A bore 214 in the sleeve 212 receives an end of the coil 12 such that the coil 12 couples to the conductor 210 within the sleeve 212. Boser et al. does contemplate additional sleeve configurations 312, 412, 512, 612, 712. Each sleeve 312, 412, 512, 612, 712, has a respective protrusion 315, 415, 515, 615, 715 which forms a groove(s) 314, 414, 514, 614, 714 for receiving the associated coil. There are also problems associated with the teachings of Boser et al. Securing the sleeve to the conductor by crimping is undesirable with helically wound conductors as damage is likely. Further, the protrusions 315, 415, 515, 615, 715 undesirably increase the profile and complexity of the lead.

A single axis coated wire design has also been used to accommodate the need for multiple components at the distal end. In this design, each filar in a multifilar coil is individually insulated from one another and wound together. Thus, this design can accommodate multiple electrodes with just one multifilar coil without significantly increasing the profile (i.e., diameter) of the lead. However, this configuration also has considerable disadvantages. There is an increased possibility of insulation breakage, especially for long-term lead implantation because the insulation around each individual filar must be extremely thin so that the filars may be wound together. Insulation breakage may result in current leaks and voltage jumps, especially when used for defibrillation. Also, leads with this configuration have a tendency to stretch, which is particularly dangerous if an implanted lead has to be removed.

A general consideration for all leads that incorporate multifilar conductor coils relates to the increase of electrical impedance due to the winding of the filars into a coil configuration. The multifilar coil typically extends through the entire length of the lead body and requires electricity to travel through relatively long wires. The significant increase in the electrical path results in a significant increase in the electrical resistance associated with the wire material. Additionally, since the lead is designed for use with an implantable device, electricity delivered to the lead would be generated via battery power. Therefore, any increase in resistance reduces electrical efficiency and the life of the battery within the implanted device.

It would be advantageous therefore to provide a multifilar conductor coil suitable for incorporation in a single lumen implantable endocardial lead which is reliable and reduces the risk of current leakage, voltage jumps, and loss of electrical integrity. The conductor should neither significantly increase the lead diameter nor stretch during lead implantation and removal. Furthermore, the conductor should minimize the total electrical impedance so as to allow a large current to pass through the lead.

SUMMARY OF THE DISCLOSURE

To provide a solution to the problems and shortcomings associated with prior art endocardial leads, there is disclosed herein a novel multifilar conductor and method of making same. The novel multifilar conductor disclosed herein includes a plurality of junctions which transition from conductor to electrode. In a lead constructed in accordance with the present disclosure, this configuration, among other things, serves to minimize the lead profile and resiliently accomplish connections between electrical components.

In particular, the present disclosure is directed to implantable cardiac lead including an elongated lead body having a proximal end and a distal end, the elongated lead body defining an axial lumen therethrough. An electrically conductive connector is operatively associated with the proximal end of the lead body and a helically wound conductor is disposed within the axial lumen and includes at least two conducting filars in electrical communication with the electrically conductive connector. A first helically wound electrode is disposed between the proximal and distal ends and radially outward of the axial lumen for delivering electrical energy to cardiac tissue and a first cylindrical support hull is disposed within the lead body radially outward of the conductor and radially inward of the first electrode, wherein a first filar of the at least two conducting filars and a filar of the first electrode are wrapped about an outer periphery of the first support hull to facilitate an electrical connection between the conductor and the first electrode. Similarly, a second helically wound electrode is disposed between the proximal and distal ends and radially outward of the axial lumen for delivering electrical energy to cardiac tissue and a second cylindrical support hull is disposed within the lead body radially outward of the conductor and radially inward of the second electrode, wherein a second filar of the at least two conducting filars and a filar of the second electrode are wrapped about an outer periphery of the second support hull to facilitate an electrical connection between the conductor and the second electrode.

These and other unique features of the implantable cardiac lead of the subject invention will become more readily apparent from the following description of the drawings taken in conjunction with the detailed description of the presently preferred embodiments.

BRIEF DESCRIPTION OF THE DRAWINGS

So that those having ordinary skill in the art to which the present disclosure appertains will more readily understand how to construct and use the multifilar conductor of the subject disclosure, and to illustrate the beneficial and novel features of the subject disclosure, reference may be had to the drawings wherein:

FIG. 2 is a side-elevational view of a preferred embodiment of a multifilar electrical conductor constructed in accordance with the present disclosure;

FIG. 2A is an enlarged localized view of the multifilar conductor coil of FIG. 2, illustrating the relationship between the active and inactive elements thereof;

FIG. 6 is a plan view of the distal portion of an endocardial lead which may incorporate the multifilar electrical conductor shown in FIG. 5 or FIG. 4;

FIG. 7 is a plan view of an endocardial lead constructed in accordance with another embodiment of the present disclosure;

FIG. 8 is a plan view of an endocardial lead constructed in accordance with another embodiment of the present disclosure;

FIG. 9 is a plan view of a low profile lead constructed in accordance with another embodiment of the present disclosure;

FIG. 9A is a cross-sectional view of the lead of FIG. 9;

FIG. 9B is an exploded plan view of the lead of FIG. 9;

Figure 1:
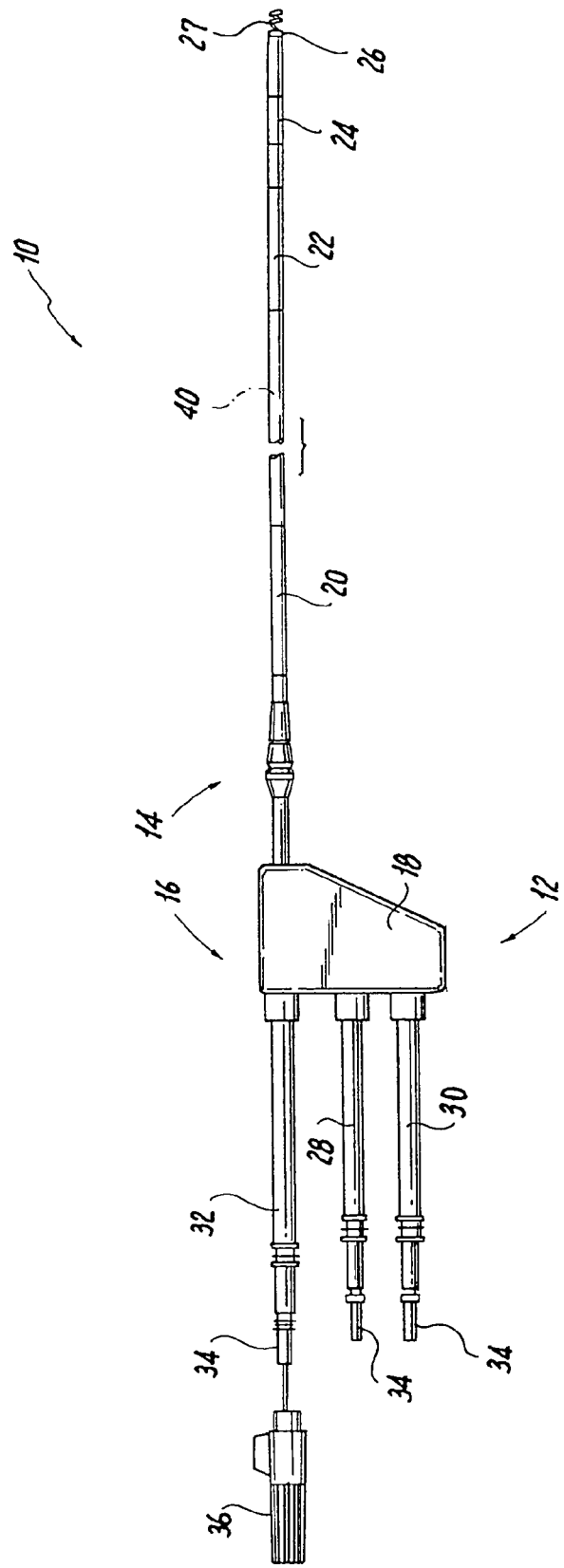
FIG. 1 is a plan view of an endocardial quadripolar defibrillation lead constructed in accordance with a preferred embodiment of the present disclosure.

These and other features of the multifilar conductor of the present disclosure and the endocardial leads incorporating the same will become more readily apparent to those having ordinary skill in the art form the following detailed description of the presently preferred embodiments.

DETAILED DESCRIPTION OF THE DISCLOSURE

In the description which follows the term "proximal" refers to the end of the endocardial lead which is farthest from the surgical site, while the term "distal" refers to the end of the lead which is intended to be closest to the heart. In addition, in the following detailed description of the disclosure, whenever possible like reference numerals arebe used to identify similar structural elements of the invention disclosed herein.

Referring now to FIG. 1, an endocardial lead fabricated in accordance with the present disclosure is indicated generally by the reference numeral 10. Lead 10 includes an elongated support body or lumen 12 having a distal end portion 14 and a proximal end portion 16. Distal end portion 14 may be straight or have a pre-formed shape, such as a J-shape. Body 12 may include various joints, spacers, extensions and adapters to increase its operational length.

The distal end portion 14 of lead body 12 houses various electrical components used for defibrillation, cardioversion and/or cardiac pacing. The proximal end portion 16 includes a yoke 18 having connectors for electrically linking proximal end portion 16 with an external device (or devices), such as a pacemaker or defibrillator, which controls and supplies power to the electrical components at distal end portion 14. Alternatively, the connectors operatively associated with proximal end portion 16 may be electrically linked with an implantable device, such as an internal pacemaker or defibrillator, for controlling and supplying power to the electrical components at distal end portion 14.

In lead 10, the distal end portion 14 includes electrical components in the form of a first (or "proximal") defibrillation coil 20 for delivering an electrical charge, a second (or "distal") defibrillation coil 22 for delivering an electrical charge, a pacing/sensing ring electrode 24, and a distal tip electrode 26 for pacing/sensing. Ring electrode 24 and tip electrode 26 provide pacing/sensing in different portions of the heart. A helical fixation screw 27 is located at the distal end portion 14 of the lead body 12 for actively securing the device at a desired location. Preferably, helical fixation screw 27 is extendable and retractable through manipulation of a driver 36 associated with proximal end portion 16. It is envisioned that fixation screw 27 is steroid-eluting in that it includes a biocompatible releasing agent contained therein or coated thereon which hastens recovery of the surrounding tissue after screw 27 is secured. Alternatively, tines may be used in place of fixation screw 27. Proximal and distal defibrillation coils 20 and 22, are preferably formed from platinum, iridium, or alloys thereof, and preferably coated with a material of low polarization, such as iridium oxide, titanium, tantalum, or alloys thereof. Preferably, all electrically active surfaces are coated with a material of low polarization., which provides for stable and low cardial stimulation thresholds and favorable sensing properties, among other things.

Yoke 18, which is operatively associated with the proximal end portion 16 of lead body 12, supports a first unipolar connector 28, a second unipolar connector 30 and a bipolar connector 32. Unipolar connectors 28 and 30 may be of the type commonly known in the art as a DF-1 Unipolar. Bipolar connector 32 may be of the type commonly known in the art as IS-1 Bipolar. Connectors 28, 30 and 32 are insulated conductors and each has a terminal end pin 34 for engaging with connector ports of another device, such as an implantable pacemaker or defibrillator. It should be understood by those skilled in the art that the connectors may comprise any suitable configuration that corresponds to the connector ports of the implanted device. In this embodiment, unipolar connector 28 is associated with proximal defibrillation coil 20, unipolar connector 30 is associated with distal defibrillation coil 22, and bipolar connector 32 is associated with ring electrode 24 and pacing/sensing electrode 26. Alternatively, all three connectors 28, 30 and 32 may be united into one connector with 3 or 4 connector electrode rings.

Referring now to FIGS. 2 and 2A, a multifilar conductor 40 provides electrical communication between the electrical components associated with the distal end portion 14 and the connectors associated with the proximal end portion 16. Conductor 40 extends longitudinally through the interior lumen of body 12. Preferably, conductor 40 is in the form of a coil conductor composed of a plurality of adjacent helically-wound elements or filars. Thus, conductor 40 has a generally cylindrical profile and circular cross-section along its latitudinal axis.

In the embodiment of FIG. 2, conductor 40 has six helically wound filars, including two electrically inactive elements 44a and 44b, and electrically active elements 46a, 46b and 48a, 48b. Elements 46a, 46b, which shall be collectively referred to hereinafter as "set 46", are adjacently wound in the coil and carry electricity of the same polarity. Likewise, elements 48a, 48b, which shall be collectively referred to hereafter as "set 48", are adjacently wound and carry electricity of the same polarity. Inactive elements 44a and 44b insulate the active elements of differing charges from one another. Thus, elements in set 46 are insulated from elements in set 48 by elements 44a and 44b which are disposed and wound between the active elements.

It is preferable to provide redundancy in the conductor 40 by utilizing more than one element in each set in the lead to lower the resistance and convey current of the same polarity in case there is a break or lapse of current in a particular element. However, sets 46 and 48 may simply include a single active element to carry current of each charge. It should be understood that is within the purview of the present disclosure to use other conductor arrangements and other numbers of active and inactive elements therein. Preferably, and as shown in FIGS. 2 and 2A, the active elements of sets 46 and 48 have an electrically insulative covering 50 to provide further electrical integrity.

The active elements of sets 46 and 48 are connected with the electrical components of the distal end portion 14. The connections may be made via any conventional means such as laser welding or crimping. The elements associated with a positive charge will be connected to pacing ring 24, and although these elements extend through body 12 to the tip electrode 26, only elements associated with a negative charge will be connected to tip electrode 26. Thus, pacing ring 24 defines an anode and tip electrode 26 defines the cathode. In addition, elements associated with a positive charge are connected with one of the defibrillation coils 20 or 22, while the elements associated with a negative charge are connected with the other defibrillation coil.

Inactive elements 44a and 44b provide greater insulation between the oppositely charged electrically active element sets 46 and 48 than prior art leads. This novel arrangement greatly improves the structural integrity and reliability of lead 10, by, among other things, preventing current leakage, voltage jumps and helping to maintain the electrical circuit should covering 50 on an active filar become torn or fractured. Since the inactive elements 44a and 44b are wound with active element sets 46 and 48 in the coil configuration, the number of revolutions of active element sets 46 and 48 required to make conductor 40 extend through body 12 is less than in prior art coil configurations. By minimizing the length of active elements 46 and 48, the distance required for electricity to travel is less. This minimizes the amount of electrical resistance in the conductor. In accordance with the present disclosure, a plurality of inactive elements may be included in the coil solely for the purpose of minimizing the overall electrical resistance of the conductor.

Inactive elements 44a and 44b may be constructed from a nonconductive biocompatible material, such as Teflon®, polyimide, polyamide (Nylon), polyurethane or other similar material. Inactive elements 44a and 44b may be in the form of a wire, strand or band. To maintain the shape of the non-conductive element and the electrically active elements, it may be necessary to include a heating or tempering process during the actual coil-winding manufacturing process. The tempering process could be also used to melt the inactive element between the active elements which would advantageously alter the stiffness, form and shape of the conductor coil. Alternatively, the inactive elements may be formed from the same wires as the active elements having insulative sheaths, but they are not used to carry a charge. Thus, they are electrically inactive.

In an exemplary embodiment of the present disclosure, the diameter D1 of conductor 40 may range from about 0.50 mm to about 2.0 mm, but is preferred to be about 0.850 mm. The diameter D2 of inactive elements 44a and 44b may range from about 0.10 mm to about 0.20 mm, but is preferred to be about 0.160 mm. The diameter D3 for active element sets 46 and 48 may range from about 0.10 mm to about 0.20 mm without covering 50, but is preferred to be about 0.126 mm. The diameter D4 for active element sets 46 and 48 including covering 50 may range from about 0.10 mm to about 0.20 mm, but is preferred to be about 0.160 mm. These dimensions are not limiting and are used merely for illustrating an embodiment of an endocardial lead constructed in accordance with the present disclosure.

Figure 3:
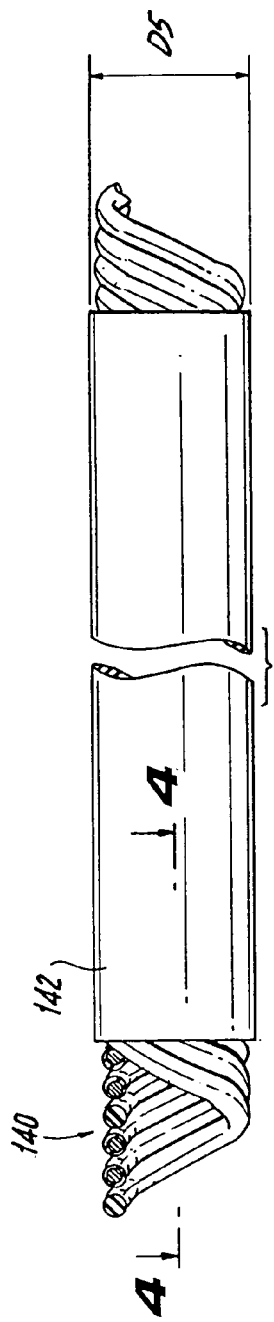
FIG. 3 is a side-elevational view of another preferred embodiment of a multifilar electrical conductor constructed in accordance with the present disclosure that includes a protective polymer sheath.
Figure 4:
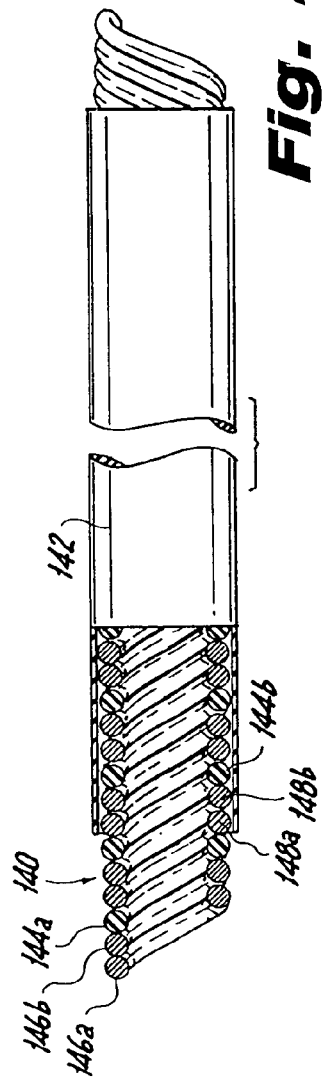
FIG. 4 is a cross-sectional view taken along line 4—4 of FIG. 3 illustrating the plurality of elements forming the electrical conductor.

Referring to FIGS. 3 and 4, there is illustrated another embodiment of a conductor fabricated in accordance with the present disclosure and designated generally by reference number 140. As will be appreciated by those of ordinary skill in the pertinent art, the following embodiments utilize the same principles as the lead 10 described above. Accordingly, like reference numerals preceded by the numeral "2", "3", "4" or "5" are used to indicate like elements whenever possible. Conductor 140 differs from conductor 40 in that it includes an insulative/protective sheath 142 defined by a covering, coating or tube disposed on the outer periphery thereof. Preferably, sheath 142 has been treated to enhance its bonding performance. Sheath 142 prevents conductor 140 from expanding in length, gives the distal end portion of the lead body a preformed memory shape, and provides resiliency and torqueability stiffness along the lead body, among other things. Sheath 142 may be made from a polymer, such as polyurethane, a mixture of silicone and polyurethane, polytetrafloroethylene (PTFE) or another thermoplastic material, and may be disposed over conductor 140 by heat shrinking or some other suitable method for adhering the polymer to conductor 140. For example, conductor 140 may be surrounded by a polyurethane tube which is adhered thereto via heat-shrinking. It is envisioned that the covering or tube may be first treated by etching, or otherwise, to further enhance bonding ability.

As shown in FIG. 4, conductor 140 is wound with two sets of active elements 146a, 146b (collectively referred to hereinafter as "set 146"), and 148a, 148b (collectively referred to hereinafter as "set 148"). Inactive elements 144a and 144b insulate the active elements in set 146 from the active elements in set 148. In an exemplary embodiment of the present disclosure depicted in FIGS. 3 and 4, the diameter D5 of conductor 140 with sheath 142 may be within the range of about 0.60 mm to about 1.20 mm, but preferably is about 0.950 mm.

Figure 5:
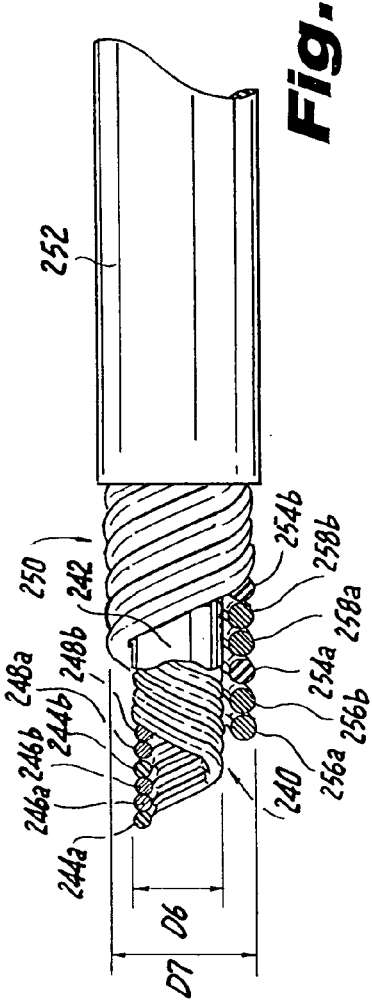
FIG. 5 is a side-elevational view of another embodiment of a multifilar electrical conductor constructed in accordance with the present disclosure having coaxially arranged inner and outer coils each having six elements.

FIGS. 5 and 6 depict an exemplary embodiment of an endocardial lead 210 constructed in accordance with the present disclosure. Lead 210 utilizes a coaxial multifilar conductor arrangement having generally concentric conductors. The inner conductor 240 has two sets of dual active elements, 246a, 246b and 248a, 248b, collectively referred to as set 246 and set 248, which are insulated from each other by two inactive elements 244a and 244b. The outer conductor 250 also has two sets of dual active elements, 256a, 256b and 258a, 258b, collectively referred to as set 256 and set 258, which are insulated from each other by two inactive elements 254a and 254b. Both conductors 240 and 250 have insulative sheaths 242 and 252, respectively, for preventing the lengthwise expansion of conductors 240 and 250, giving the distal end portion of the lead body a preformed memory shape, and providing resiliency and torqueability along the lead body, among other things.

For purposes of illustrating the exemplary arrangement in more detail, elements in set 246 of inner conductor 240 and elements in set 256 of outer conductor 250 have been arbitrarily designated as positively charged. Similarly, elements in set 248 of inner conductor and elements in set 258 of outer conductor 250 are designated as negatively charged for purposes of this illustration. Thus, a preferable arrangement would have elements in set 248 connecting with tip electrode 226, elements in set 246 connecting with pacing ring 224, elements in set 256 connecting with distal defibrillation coil 222, and elements in set 258 connecting with proximal defibrillation coil 220.

In an exemplary embodiment of the present disclosure illustrated in FIGS. 5 and 6, inner conductor 240 has a outer diameter D6 which includes a sheath 242 substantially similar to sheath 142 shown in the embodiment of FIGS. 3 and 4. Outer conductor 250 has an outer diameter D7 not including sheath 252. D6 may range from about 0.50 mm to about 1.00 mm, but is preferred to be about 0.950 mm, while D7 may range from about 1.20 mm to about 1.60 mm, but is preferred to be about 1.27 mm. It is preferable that conductors 240 and 250 are suitably sized so that the interior portion of conductor 250 is disposed against the sheath 242 on conductor 240. This configuration serves to enhance the structural integrity, tensile strength and insulative properties of the lead, among other things.

Figure 7A:
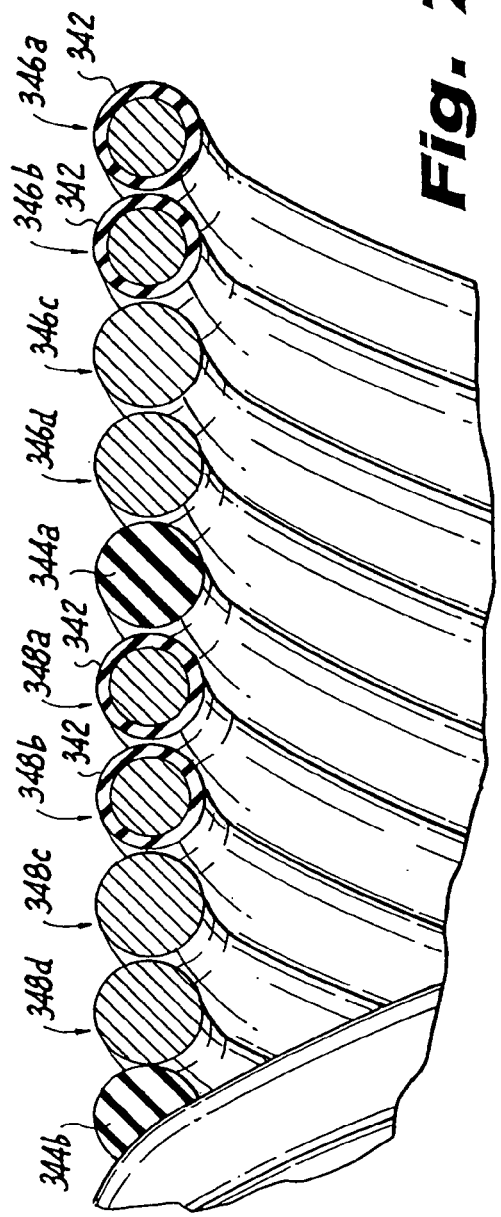
FIG. 7A is an enlarged localized view of the multifilar conductor coil of FIG. 7, illustrating the relationship between the active and inactive elements thereof.

In another embodiment illustrated in FIGS. 7 and 7A, the lead 310 has conductor 340 with two sets of four active elements 346a–d and 348a–d, collectively referred to as set 346 and set 348, which are insulated from each other by two inactive elements 344a and 344b. Conductor 340 has insulative sheaths 342 covering active elements 346a, 346b in set 346 and 348a, 348b in set 348. Active elements 346c, 346d in set 346 and 348c, 348d in set 348 are uncovered. Thus, elements 346c, 346d, 348c and 348d administer defibrillation shocks in area 320 on the distal portion 314 without the need for a separate defibrillation providing apparatus. The remaining two insulated active elements in sets 346 and 348 (i.e., elements 346a, 346b, 348a and 348b), are operatively associated with electrode tip 326 at distal end portion 314.

Figure 8A:
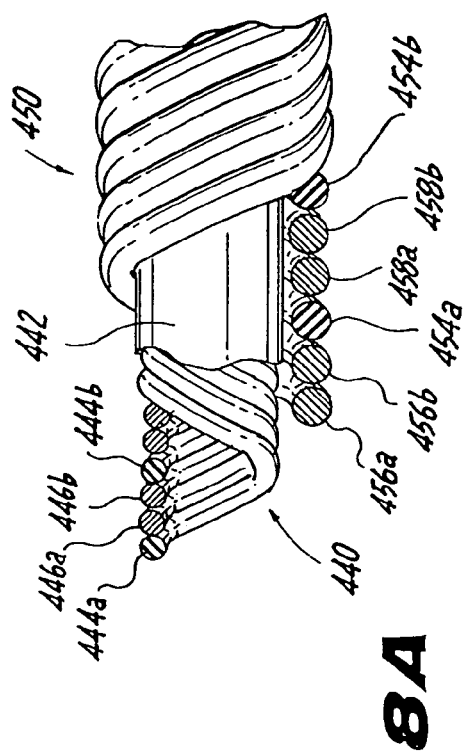
FIG. 8A is an enlarged localized view of the multifilar conductor coil of FIG. 8, illustrating the relationship between the inner and outer conductors and the active and inactive elements thereof.

In another embodiment illustrated in FIGS. 8 and 8A, the lead 410 uses a coaxial multifilar conductor arrangement having inner conductor 440 and outer conductor 450. Much like the embodiment illustrated in FIGS. 5 and 6, the inner conductor 440 has two sets of dual active elements 446a, 446b, 448a and 448b, collectively referred to as set 446 and set 448, respectively, which are insulated from each other by two inactive elements 444a and 444b. The outer conductor 450 also has two sets of dual active elements 456a, 456b, 458a and 458b, collectively referred to as set 456 and set 458, respectively, which are insulated from each other by two inactive elements 454a and 454b. Inner conductor 440 has insulative sheath 442 disposed thereon which electrically insulates inner conductor 440 from outer conductor 450. Alternatively, or in combination with sheath 442, the active elements in set 446 and set 448 may be insulated. Defibrillation shocks are administered by active elements in set 456 and set 458 which are exposed in areas 420 and 422 on the distal portion 414 without the need for a separate defibrillation providing apparatus. Inner conductor 440 is operatively associated with electrode tip 426 at distal end portion 414.

Referring now to FIGS. 9A–9E, there is a particular embodiment 510 similar to the type shown in FIG. 8 having two defibrillator/shocking coils and a pacing/sensing lead. The lead 510 differs from the previous embodiments in that lead 510 includes low profile junctions for integrating active components such as defibrillation coils and pacing/sensing leads into the lead body. The junctions facilitate resilient electrical connection between the conductor coils and electrodes while not unduly increasing the profile of the lead 510. Further, only a single lumen is required for multiple active components. It will be appreciated by those of ordinary skill in the pertinent art that the improved junction of lead 510 can be easily utilized with the previous embodiments or other leads to obtain the advantages discussed herein. Although not shown for simplicity, the proximal end portion of lead 510 includes one or more connectors for electrically linking proximal end portion with an external device (or devices), such as a pacemaker or defibrillator, similar to that shown in FIGS. 1, 7 and 8 or in any of numerous configurations known to one of ordinary skill in the pertinent art.

The lead 510 includes several pieces of tubing 530, 532, 534, 536, and 538 for defining a single lumen 512 that extends throughout the lead 510. The lead 510 also includes defibrillation electrodes 520, 522 and a unipolar pacing/sensing electrode 526 at the distal end. In a preferred embodiment, the defibrillation electrodes 520, 522 take the form of contact coils and are interchangeably described as such herein. A lead coil 540 passes through the single lumen 512 and operatively connects the contact coils 520, 522 and pacing/sensing electrode 526. A series of junctions 542, 544, 546, 548, 550 connect the tubing 530, 532, 534, 536, 538, and operatively interconnect the contact coils 520, 522 with the lead coil as described hereinbelow with respect to FIGS. 9C–E.

It is envisioned that the lead coil 540 is a multifilar helically wound coil but may be any of numerous configuration as would be appreciated by those of ordinary skill in the pertinent art based upon review of the subject disclosure. Preferably, the filars of the lead coil 540 are either MP35N or DFT/MP35N, each filar having a polyimide coating. MP35N is a medical grade multiphase nimonic alloy primarily composed of 20% chromium, 35% cobalt, 10% molybdenum and 35% nickel.

The distal end of lead 510 includes a steroid-eluting ring 552. An exemplary ring 552 is disclosed in U.S. patent application Publication No. 2003/0093136, published on May 15, 2003, which is incorporated herein by reference in its entirety. The distal end of lead 510 also includes a tip assembly 554. The tip assembly 554 has a helical fixation screw 527 that secures the lead 510 at a desired location.

Figure 9C:
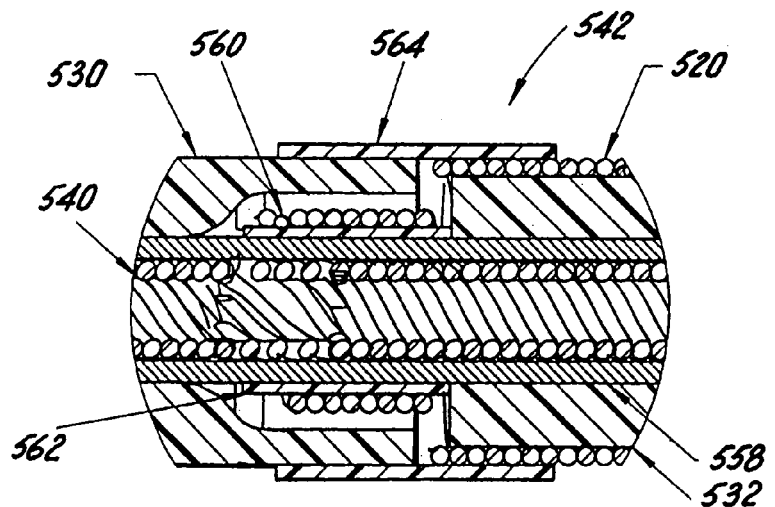
FIG. 9C is an enlarged localized view of a junction of the lead of FIG. 9, illustrating the interconnection between the lead coil and first electrode.

Referring now to FIG. 9C, at junction 542 a proximal portion of the lead coil 540 is coupled with contact coil 520. Although an insulative protective sheath 558 surrounds the lead coil 540 in the area of the junction 542, at least one filar 560 for providing power to the contact coil 520 passes through the sheath 558 and wraps around an outer periphery of an electrically conductive hull 562 to facilitate connection to the contact coil 520. The hull 562 is disposed within the central lumen 512 radially outward of the lead coil 540 and sheath 558, and radially inward of the contact coil 520. The contact coil 520 also wraps around the outer periphery of the hull 562. A contact spacer tubing 532 concentric with and radially inward of the contact coil 520 provides rigidity to the remaining portion of the contact coil 520 which is not supported by the hull 562. Preferably, the end of the filar of the lead coil 540 and the end of the filar of the contact coil 520 are adjacent on the support hull 562 so that direct electrical connection can be made between the two filars by removing a portion of the respective filars insulation and welding the two filars together.

In another embodiment, the hull 562 is not electrically conductive. In still another embodiment, several turns of each filar from the lead coil 540 and the contact coil 520 are adjacent one another. In another embodiment, the filars of the lead coil 540 and contact coil 520 are not adjacent but attached to the hull 562 so that the conductivity of the hull 562 completes the electrical connection. The filars of the lead coil 540 and contact coil 520 may be secured to the hull 562 by welding and the like as would be appreciated by those of ordinary skill in the pertinent art. In a preferred embodiment, the lead coil 540 has nine filars of which two are wrapped around and welded to the hull 562. A third filar serves as insulation between the two live filars. The remaining filars of the lead coil 540 extend through the junction 542 within the single central lumen 512.

A tubing seal 564 retains the tubing 530 in relation to the contact spacer tubing 532 and further insures that the contact coil 520 remains in place and does not buckle over the tubing 530. Preferably, the tubing seal 564 is formed of silicone that expands in hexane and shrinks when hexane evaporates. Thus, in hexane, the tubing seal 564 slides over the lead 510 to the junction 542. As the hexane evaporates, the tubing seal 564 shrinks securely onto an outer periphery of the junction 542. In alternate embodiments, the tubing seal 564 may attach by an interference fit, heat shrink-wrapping, glue, crimping and other suitable techniques known to those of ordinary skill in the pertinent art. Tubing 530 substantially surrounds the lead coil 540 but at the junction 542, tubing 530 also surrounds the hull 562, and nearly abuts the contact spacer tubing 532. Accordingly, at junction 542 the lead coil 540 operatively connects to the contact coil 520 in a resilient low-profile manner. In a preferred embodiment, junction 546 is similar to junction 542 and, for simplicity, is not further described herein.

Figure 9D:
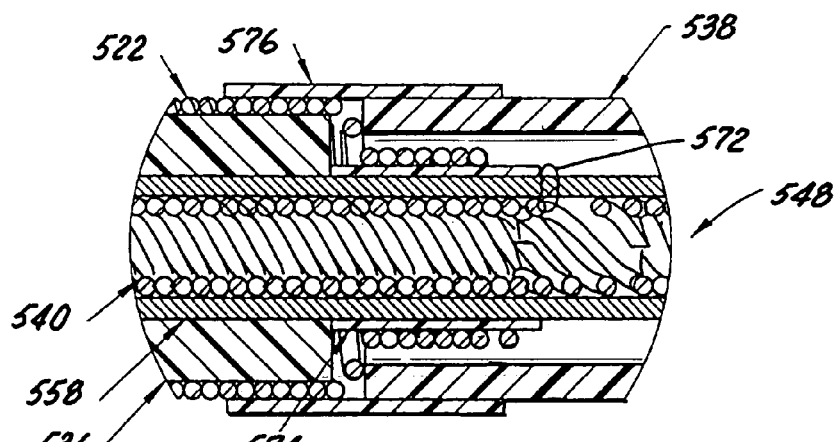
FIG. 9D is an enlarged localized view of a junction of the lead of FIG. 9, illustrating the interconnection between the lead coil and second electrode.

Referring now to FIG. 9D, at junction 548 lead coil 540 is operatively connected to contact coil 522. Sheath 558 surrounds the lead coil 540 in the area of the junction 548 so that the filar 572, acting as return from the contact coil 522, passes through the sheath 558 and wraps around a conductive hull 574 to facilitate electrical connection. The hull 574 is disposed within the central lumen 512 radially outward of the lead coil 540 and sheath 558 and radially inward of the contact coil 522. Preferably, the lead coil 540 and contact coil 522 are secured and electrically connected to the hull 574 by welding. The remaining filars of the lead coil 540 extend through the junction 548 within the single central lumen 512. Additional retention is provided by a shrink-wrap tubing seal 576 that slides over junction 548. A contact spacer tubing 536 concentric with and within the contact coil 522 provides rigidity to the remaining portion of the contact coil 522 that is not supported by the hull 574. In an alternate embodiment, contact spacer tubing 536 is monolithic with contact spacer 532. Tip cover tubing 538 substantially surrounds the lead coil 540 but at the junction 548, tubing 538 also surrounds the hull 574, and nearly abuts the contact spacer tubing 536. Accordingly, junction 548 operatively connects the lead coil 540 to contact coil 522 in a resilient low-profile manner. In a preferred embodiment, junction 544 is similar to junction 548 and, for simplicity, is not further described herein.

Figure 9E:
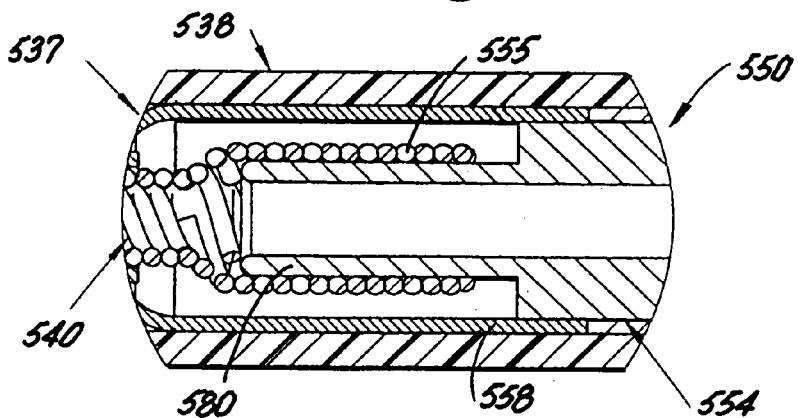
FIG. 9E is an enlarged localized view of a junction of the lead of FIG. 9, illustrating the interconnection between the lead coil and tip assembly.

Referring now to FIG. 9E, at junction 550 lead coil 540 is operatively connected to tip assembly 554. Preferably, the lead coil 540 is connected and secured to the tip assembly 554 by wrapping the filars 555 around the inner hull 580 of the tip assembly 554 and then welding the filars 555 thereto. Sheath 537 surrounds the lead coil 540 throughout the junction 550. In a preferred embodiment, sheath 537 is monolithic with sheath 558. Tubing tip cover 538 encases the junction 550. Accordingly, junction 550 operatively connects the lead coil 540 to the tip assembly 554 in a resilient low-profile manner.

In summary, the junctions 542, 544, 546, 548, 550 are examples of resilient low profile connections between active components and a single helically wound conductor coil. Although the preferred embodiments are described in connection with defibrillation coils and pacing/sensing leads for a single lumen lead, the advantageous may be equally realized for multiple lumen leads and for active components now known and later developed. For example, variations of the junctions according to the present disclosure can be adapted to minimize the electrical resistance, improve upon the electrical integrity of the lead, and minimize the profile. For additional examples, leads constructed in accordance with the subject disclosure may of course be used in conjunction with leads having a greater or fewer number of filars, electrodes, connectors and conductors. Therefore, while the invention has been described with respect to preferred embodiments, those skilled in the art will readily appreciate that various changes and/or modifications can be made to the invention without departing from the spirit or scope of the invention as defined by the appended claims.

What is claimed is:

1. A low profile implantable cardiac lead, comprising:
   a) an elongated lead body having a proximal end portion and a distal end portion, the elongated lead body having an axial lumen therethrough;
   b) an electrically conductive connector operatively associated with the proximal end of the lead body;
   c) a helically wound conductor coil disposed within the axial lumen of the lead body and including at least two conducting filars in electrical communication with the electrically conductive connector;
   d) at least one helically wound defibrillation coil disposed between the proximal and distal end portions and radially outward of the axial lumen for delivering electrical energy to cardiac tissue;
   e) at least one cylindrical support hull disposed within the lead body radially outward of the conductor coil and radially inward of the at least one defibrillation coil, wherein a filar of the at least two conducting filars and a filar of the at least one defibrillation coil are wrapped about an outer periphery of the at least one support hull to facilitate an electrical connection between the at least one conductor and the at least one defibrillation coil; and
   f) a tip assembly connected to the distal end portion of the lead body and in electrical communication with the conductor coil, the tip assembly having a pacing ring electrode.

2. A low profile implantable cardiac lead as recited in claim 1, wherein the at least one support hull is electrically conductive.

3. A low profile implantable cardiac lead as recited in claim 1, wherein at least one filar of the conductor coil and a filar of the at least one defibrillation coil are welded to the support hull, respectively.

4. A low profile implantable cardiac lead as recited in claim 1, wherein at least one filar of the conductor coil is welded to a filar of the at least one defibrillation coil for completing an electrical connection therebetween.

5. A low profile implantable cardiac lead as recited in claim 1, further comprising a cylindrical seal radially outward of the at least one defibrillation coil to secure the first defibrillation coil in place and prevent buckling thereof.

6. A low profile implantable cardiac lead as recited in claim 1, further comprising a sheath radially outward of the conductor and radially inward of the support hulls for providing insulation and strength in the lead body.

7. A low profile implantable cardiac lead as recited in claim 6, wherein the sheath is formed from a heat shrinkable polymer tube.

8. A low profile implantable cardiac lead as recited in claim 1, further comprising: a second helically wound defibrillation coil disposed between the proximal and distal end portions and radially outward of the axial lumen for delivering electrical energy to cardiac tissue; and a second cylindrical support hull disposed within the lead body radially outward of the conductor and radially inward of the second defibrillation coil, wherein a second filar of the at least two conducting filars and a filar of the second defibrillation coil are wrapped about an outer periphery of the second support hull to facilitate an electrical connection between the conductor and the second defibrillation coil.

9. A low profile implantable cardiac lead as recited in claim 8, further comprising a second cylindrical seal radially outward of the second defibrillation coil to secure the second defibrillation coil in place.

10. A low profile implantable cardiac lead as recited in claim 8, wherein the conductor has three filars for connecting to the at least one defibrillation coil, three filars for connecting to the second defibrillation coil and three filars for connecting to the pacing ring electrode.

11. A low profile implantable cardiac lead as recited in claim 1, further comprising helical fixation screw connected to the tip assembly for attaching the lead body to cardiac tissue.

12. A low profile implantable cardiac lead as recited in claim 11, further comprising a steroid-eluting ring coupled to the tip assembly for hastening recovery of the cardiac tissue.

13. A low profile assembly for delivering electrical energy to cardiac tissue, comprising:
    first means having a proximal end and a distal end, the first means for defining an axial lumen therethrough:
    a multifilar coil extending through the lumen for carrying electrical energy;
    third means disposed between the proximal end and the distal end and radially outward of the axial lumen for contacting cardiac tissue; and
    fourth means disposed within the axial lumen for facilitating an electrical connection between the niultifilar coil and third means, the fourth means having an inner wall radially outward of the multifilar coil and an outer wall radially inward of the third means wherein portions of the multifilar coil and third means are coupled to the outer wall of the fourth means.

14. A low profile assembly as recited in claim 13, wherein the first means is an elongated lead body.

15. A low profile assembly as recited in claim 13, wherein the third means is a helically wound defibrillation coil.

16. A low profile assembly as recited in claim 13, wherein the fourth means is a hull.

17. A low profile assembly as recited in claim 13, wherein the portion of the muttifilar coil is welded to the portion of the third means.

18. A low profile cardiac lead having a helically wound conductor and a helically wound electrode, the cardiac lead comprising: a cylindrical support hull disposed within a lumen of the cardiac lead, the support hull being disposed radially outward of the conductor and radially inward of the electrode, wherein filars of the conductor and filars of the electrode, respectively, are wrapped about an outer periphery of the support hull to facilitate an electrical connection between the conductor and electrode.

19. A low profile cardiac lead as recited in claim 18, wherein the filars of the conductor and electrode are welded to the support hull.

20. A low profile cardiac lead as recited in claim 19, wherein the support hull is electrically conductive.

21. A low profile cardiac lead as recited in claim 18, further comprising a cylindrical seal radially outward of the electrode to prevent buckling of the electrode.

22. A low profile cardiac lead as recited in claim 18, further comprising an insulative sheath radially outward of the conductor and radially inward of the hull.

* * * * *